(12) United States Patent
Sasai et al.

(10) Patent No.: US 12,053,335 B2
(45) Date of Patent: Aug. 6, 2024

(54) HOLDING DEVICE

(71) Applicant: OLYMPUS CORPORATION, Tokyo (JP)

(72) Inventors: Ryota Sasai, Hachioji (JP); Masafumi Haraguchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 526 days.

(21) Appl. No.: 17/337,559

(22) Filed: Jun. 3, 2021

(65) Prior Publication Data

US 2021/0282889 A1  Sep. 16, 2021

Related U.S. Application Data

(63) Continuation of application No. PCT/JP2018/044993, filed on Dec. 6, 2018.

(51) Int. Cl.
*A61B 90/50* (2016.01)
*F16M 13/02* (2006.01)

(52) U.S. Cl.
CPC ............ *A61B 90/50* (2016.02); *F16M 13/02* (2013.01); *A61B 2090/508* (2016.02); *F16M 2200/021* (2013.01); *F16M 2200/066* (2013.01)

(58) Field of Classification Search
CPC .. A61B 90/50; A61B 2090/508; F16M 13/02; F16M 2200/021; F16M 2200/066
USPC ...................................................... 248/277.1
See application file for complete search history.

(56) References Cited

U.S. PATENT DOCUMENTS

| | | | | |
|---|---|---|---|---|
| 7,841,979 | B2 * | 11/2010 | Hirose | A61B 10/00 600/101 |
| 8,661,645 | B2 * | 3/2014 | Lemser | G01M 17/021 73/146 |
| 11,446,115 | B2 * | 9/2022 | Haraguchi | A61B 1/3132 |
| 2002/0100851 | A1 | 8/2002 | Abramowsky et al. | |
| 2005/0075536 | A1 * | 4/2005 | Otsuka | A61B 90/50 600/102 |
| 2012/0205558 | A1 * | 8/2012 | Jindal | G03F 7/70925 355/77 |
| 2013/0205558 | A1 | 8/2013 | Sporer et al. | |
| 2020/0121416 | A1 * | 4/2020 | Sasai | A61B 1/00121 |

FOREIGN PATENT DOCUMENTS

| | | |
|---|---|---|
| JP | 2002-206612 A | 7/2002 |
| JP | 2004-242942 A | 9/2004 |
| JP | 2013-531545 A | 8/2013 |

OTHER PUBLICATIONS

International Search Report dated Mar. 5, 2019 issued in PCT/JP2018/044993.

* cited by examiner

*Primary Examiner* — Todd M Epps
(74) *Attorney, Agent, or Firm* — Scully, Scott, Murphy & Presser, P.C.

(57) ABSTRACT

A holding device is a holding device that holds the medical device, and includes an arm configured to have a holder, which holds the medical device, at a distal end, a base configured to rotatably support the arm by a first joint, a disk attached to the arm, and a brake attached to the base and configured to press the disk, in which a distance between a center of rotation of the disk and a region where the brake presses the disk is changed depending on a rotation angle of the first joint.

9 Claims, 10 Drawing Sheets

HOLDING DEVICE

The present invention relates to a holding device including a braking mechanism.

This application is a continuation application based on PCT Patent Application No. PCT/JP2018/044993, filed Dec. 6, 2018, claiming priority the contents of which are incorporated herein by reference.

BACKGROUND

In the related art, a holding device capable of holding a medical device or the like at an arbitrary position has been used. Some holding devices do not have a drive system such as a motor, and an operator manually changes a position of a medical device or the like. The holding device needs to have a mechanism (for example, an articulated mechanism) for holding the medical device in a movable manner and a function (for example, a braking mechanism such as a brake mechanism) for fixing the medical device at an arbitrary position.

An articulated medical device holding device described in Japanese Unexamined Patent Application, First Publication No. 2004-242942 is a holding device that can hold a medical device at an arbitrary position. The articulated medical device holding device has a brake mechanism that fixes each joint of multiple joints of the medical device so that a position of the medical device is not changed when an external force is applied to the medical device to be held. Since the brake mechanism can fix all joints by a handle operation, an operator can fix all joints with one operation without a help of other operators.

SUMMARY

A holding device according to a first aspect is a holding device for holding a medical device, the holding device including: an arm having a holder positioned at a distal end of the arm and configured to hold the medical device; a base configured to rotatably support the arm by a first joint; a disk attached to the arm; and a brake attached to the base and configured to press the disk, in which a distance between a rotation center of the disk and a region where the brake presses the disk is changed depending on a rotation angle of the first joint.

According to a second aspect, in the holding device according to the first aspect, when the disk moves the arm in a direction in which the holder approaches the base, the brake may be disposed at a position where the distance increases as the first joint rotates in a direction of rotation.

According to a third aspect, in the holding device according to the first aspect, the distance may be changed in proportion to the rotation angle of the first joint.

According to a fourth aspect, in the holding device according to the first to third aspect, the holding device may be configured to hold the medical device so as to be turnable with respect to a body wall when the medical device may be inserted into a body.

According to a fifth aspect, in the holding device according to the fourth aspect, the brake may be disposed at a position where the distance increases according to an angle between a normal line from the body wall and a longitudinal axis of the medical device at a pivot point which is a turning center.

According to a sixth aspect, in the holding device according to the fourth aspect, the brake may be disposed at a position where the distance increases according to an amount of insertion when the medical device is inserted into the body by the arm.

According to a seventh aspect, in the holding device according to the fourth aspect, the medical device may be inserted into the body via a trocar.

According to an eighth aspect, in the holding device according to the fifth aspect, the pivot point may be an insertion point of the body wall.

According to a ninth aspect, in the holding device according to the first aspect, the arm may further include a second joint disposed between the holder and the first joint.

A holding device according to a tenth aspect, a holding device including: a base; an arm rotatably supported by the base and configured to hold a medical device at a distal end part of the arm; and a brake attached to the base and configured to vary a braking force of limiting a rotation of the arm in accordance with a rotation state of the arm.

According to an eleventh aspect of the holding device according to the tenth aspect, the arm may include a holder holding the medical device such that the medical device is configured to turn with respect to a body wall when the medical device is inserted through the body wall.

According to a twelfth aspect, in the holding device according to the tenth aspect, the brake may be configured to vary the braking force in accordance with an angle between a normal line from the body wall and a longitudinal axis of the medical device at a pivot point which is a turning center.

According to a thirteenth aspect, in the holding device according to the tenth aspect, as the angle becomes larger, the braking force of the brake may become large. According to a fourteenth aspect, in the holding device according to the tenth aspect, the pivot point may be an insertion point of the body wall into which the medical device is inserted.

According to a fifteenth aspect, an actuation method of a holding device including a base and an arm configured to be rotatable with respect to the base, and holding a medical device which is insertable into a body wall such that the medical device is held at a distal end of the arm. The actuation method comprising step of braking a rotation of the arm in accordance with an angle between a normal line from the body wall and a longitudinal axis of the medical device at an insertion point of the body wall into which the medical device is inserted.

According to a sixteenth aspect, in the actuation method of the holding device according to the fifteenth aspect, as the angle becomes larger, a braking force of the brake braking a rotation of the arm may vary.

DETAILED DESCRIPTION OF EXEMPLARY EMBODIMENTS

First Embodiment

A holding device according to a first embodiment will be described with reference to FIGS. 1 to 5.

Figure 1:
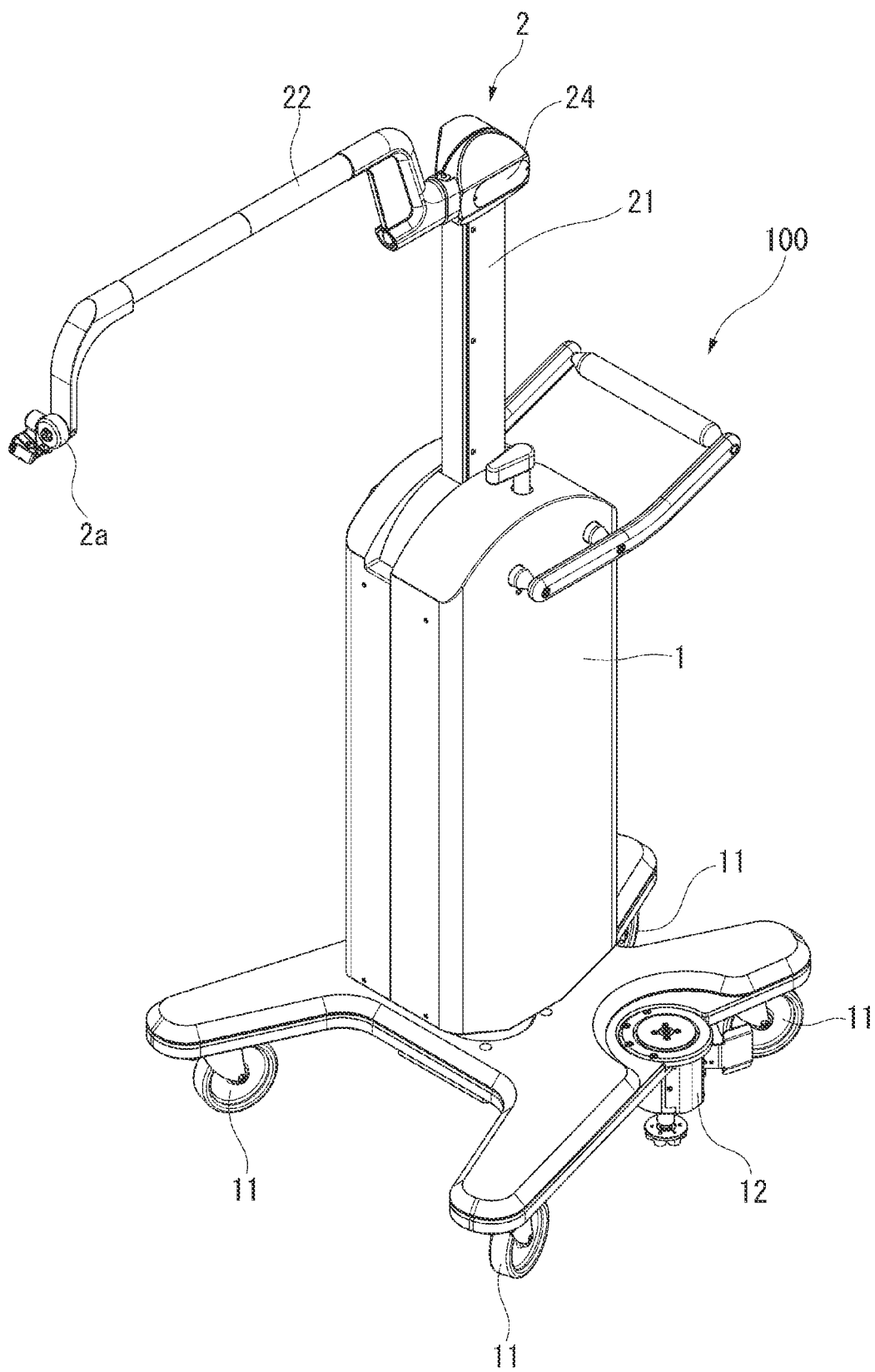
FIG. 1 is a view showing an overall configuration of a holding device according to a first embodiment.

FIG. 1 is a view showing an overall configuration of a holding device 100 according to the present embodiment. The holding device 100 includes a base 1, an arm 2, and a braking mechanism 3.

[Base 1]

As shown in FIG. 1, the base 1 is installed on a floor via rollers 11 and supports the arm 2 to be rotatable. The base 1 has a lock mechanism 12. When the lock mechanism 12 is not activated, the rollers 11 are capable of rotating and the base 1 is capable of moving on the floor. When the lock mechanism 12 is activated, the rollers 11 is restricted to rotate and the base 1 cannot move on the floor. By activating the lock mechanism 12 of the base 1, a position of the base 1 is capable of being fixed so that the position of the base 1 does not move even when the arm 2 is manually moved.

[Arm 2]

The arm 2 has a link arm 21, a distal arm 22, a first joint 23, and a second joint 24. The first joint 23 rotatably connects the link arm 21 and the base 1. The second joint 24 rotatably connects the link arm 21 and the distal arm 22. A rotation axis of the first joint 23 and a rotation axis of the second joint 24 are parallel to each other. The arm 2 is a so-called two-degree-of-freedom arm mechanism having two joints.

In the following description, in both end portions of the arm 2, one end portion of the arm 2 connected to the base 1 is referred to as a "proximal end", and the other end portion on a side opposite the proximal end is referred to as a "distal end".

The link arm (first arm) 21 is rotatably supported by the base 1 by the first joint 23 at a proximal end. The link arm 21 is connected to the distal arm 22 by a second joint 24 at a distal end.

The distal arm (second arm) 22 has a holder 2$a$ at a distal end of the distal arm 22. The holder 2$a$ is capable of holding a medical device. The holder 2$a$ is capable of holding a medical device such as an endoscope having an imaging function or a treatment tool of a gripping mechanism or the like. The medical device is held in the holder 2$a$ so as to be rotatable in a horizontal direction and a vertical direction about the holder 2$a$. The surgeon can rotate the medical device so that the medical device faces an intended direction. The distal arm 22 is connected to the link arm 21 by a second joint 24 at a proximal end.

[Braking Mechanism 3]

The braking mechanism 3 is a disk brake mechanism having a disk 31 attached to the link arm 21 and a brake 32 attached to the base 1.

Figure 2:
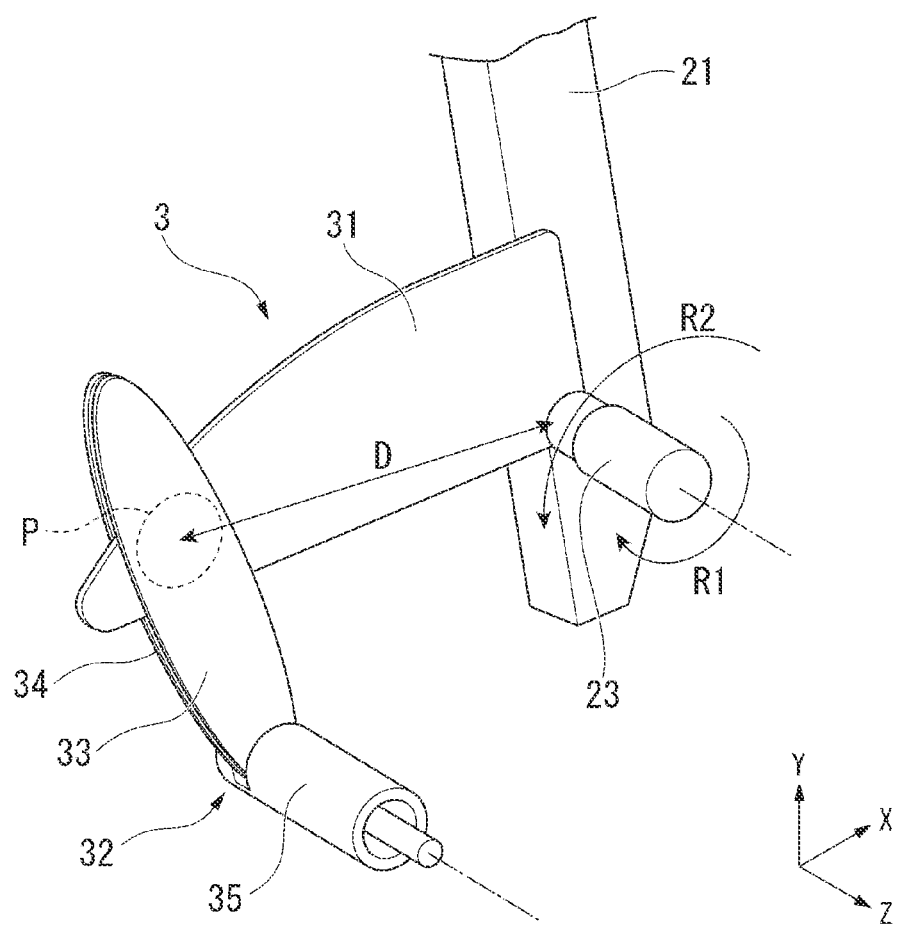
FIG. 2 is a perspective view of a first joint and a braking mechanism of the holding device.

FIG. 2 is a perspective view of the first joint 23 and the braking mechanism 3.

The disk 31 is a plate-shaped member having a disk first surface 31$a$ and a disk second surface 31$b$ on both surfaces. The disk 31 is attached to the link arm 21. The disk 31 rotates together with the link arm 21 with the first joint 23 as a center of rotation. The disk 31 is attached to the link arm 21 so that a plate thickness direction coincides with a direction of a rotation axis of the first joint 23.

In the following description, a vertical direction is defined as a Y-axis direction, and directions of the rotation axes of the first joint 23 and the second joint 24 are defined as a Z-axis direction. A direction perpendicular to the Y-axis direction and the Z-axis direction is defined as the X-axis direction. A direction in which the first joint 23 and the second joint 24 rotate when the arm 2 is moved in a direction in which the holder 2$a$ at a distal end of the distal arm 22 approaches the base 1 is referred to as a first rotation direction R1. A direction in which the first joint 23 and the second joint 24 rotate when the arm 2 is moved in a direction in which the holder 2$a$ at the distal end of the distal arm 22 is moved away from the base 1 is referred to as a second rotation direction R2.

As shown in FIG. 2, the disk 31 has an elliptical fan shape in which a portion of an elliptical shape whose center is located at the first joint 23 is cut out when viewed in the plate thickness direction (Z-axis direction). In the elliptical fan shape of the disk 31, a distance from the first joint 23 (a center of the ellipse) to the arc increases along the second rotation direction R2.

The brake 32 sandwiches the disk first surface 31$a$ and the disk second surface 31$b$ of the disk 31 from both surfaces, and brakes the rotation of the link arm 21 to which the disk 31 is attached. The brake 32 has a first brake pad 33, a second brake pad 34, and a biasing unit 35.

Figure 3:
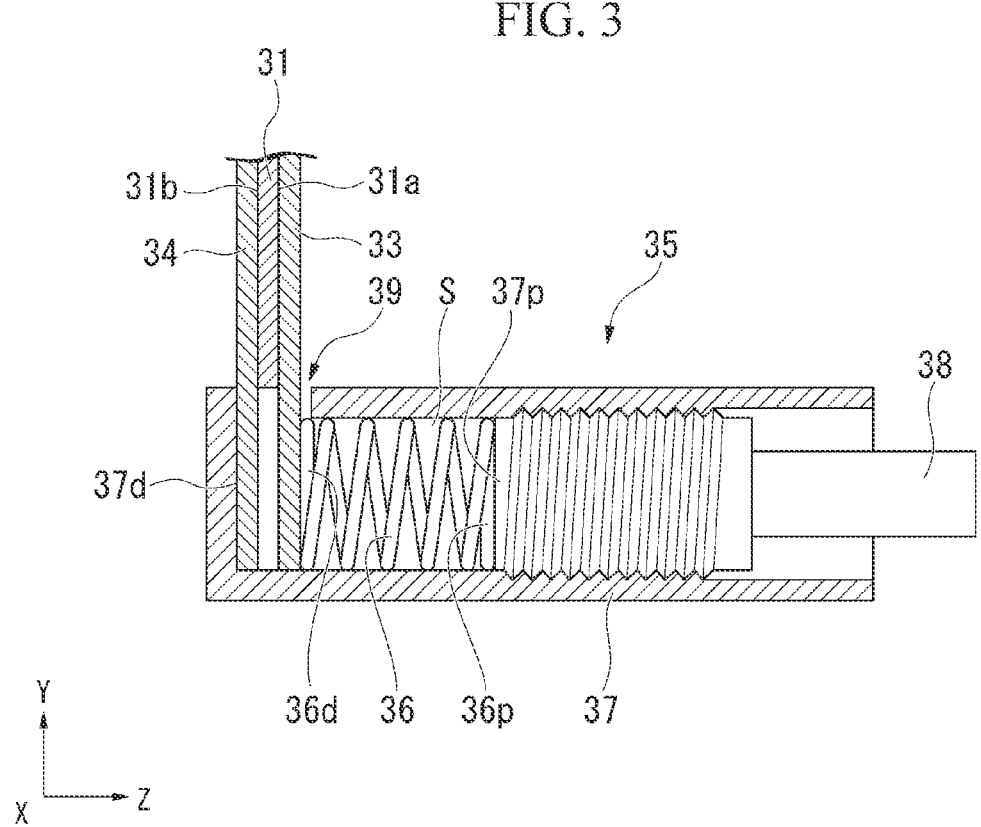
FIG. 3 is a cross-sectional view of a brake of the holding device.

FIG. 3 is a cross-sectional view of the brake 32.

The first brake pad 33 and the second brake pad 34 sandwich the disk 31 from both surfaces in the plate thickness direction (Z-axis direction). The first brake pad 33 and the second brake pad 34 are biased in a direction in which the first and second brake pad 33 and 34 approach each other by the biasing unit 35.

The first brake pad 33 comes into surface contact with the disk first surface 31$a$ of the disk 31 and brakes the rotation of the disk by a frictional force.

The second brake pad 34 comes into surface contact with the disk second surface 31$b$ of the disk 31 and brakes the rotation of the disk by a frictional force.

The biasing unit 35 has a spring 36 and a case 37 that accommodates the spring 36. The biasing unit 35 biases the first brake pad 33 and the second brake pad 34 by a restoring force of the spring 36 accommodated in an internal space S of the case 37 in a contracted state. A direction in which the spring 36 expands and contracts is a longitudinal direction of the case 37.

The case 37 is a cylindrical case that accommodates the spring 36, and has an adjusting mechanism 38, which adjusts a biasing force of the spring 36, at one end portion in the longitudinal direction. In the following description, in the longitudinal direction of the case 37, a side where the adjusting mechanism 38 is located is referred to as a "proximal end side", and a side opposite to the proximal end side is referred to as a "distal end side".

The case 37 has an opening 39 on a side surface on the distal end side. As shown in FIG. 3, a portion of the first brake pad 33 and the second brake pad 34 sandwiching the disk 31 from both surfaces is sandwiched into the opening 39 of the case 37 in a state where the plate thickness direction of the disk 31 with the longitudinal direction of the case 37 are aligned.

In the case 37, a surface opposite to a surface of the first brake pad 33, which is in surface contact with the disk first surface 31a, is in contact with a spring distal end portion 36d which is a distal end portion of the spring 36.

In the case 37, a surface opposite to a surface of the second brake pad 34, which is in surface contact with the disk second surface 31b, is in contact with a case distal end portion 37d which is a distal end portion in the internal space S of the case 37.

The spring proximal end portion 36p, which is a proximal end portion of the spring 36, is in contact with a case proximal end portion 37p, which is a proximal end portion in the internal space S of the case 37.

The spring distal end portion 36d presses the first brake pad 33 toward the distal end side by the biasing force of the spring 36. The spring proximal end portion 36p presses the case proximal end portion 37p toward the proximal end side by the biasing force of the spring 36. As a result of the case 37 being pressed toward the proximal end side by the spring 36, the case distal end portion 37d presses the second brake pad 34 toward the proximal end side. That is, the restoring force of the spring 36 is converted into a force, by which the first brake pad 33 and the second brake pad 34 press the disk 31 from both surfaces, by the case 37.

As shown in FIG. 3, the adjusting mechanism 38 is constituted by a male screw, and a position of the case proximal end portion 37p in the longitudinal direction is capable of being adjusted by adjusting a screwing position with a female screw formed inside the case 37. The adjusting mechanism 38 adjusts, a length of the spring 36 accommodated in the case 37 in an expansion-contraction direction by adjusting the position of the case proximal end portion 37p, and thus, the biasing force of the spring 36 is capable of being adjusted.

The brake 32 is attached to the base 1. A relative position between the brake 32 and the first joint 23 attached to the base 1 is not changed. Even when the link arm 21 rotates about the first joint 23 within an assumed range of use, the brake 32 is disposed at a position (a) where the biasing unit 35 does not come into contact with the disk 31, a position (b) where the first brake pad 33 and the second brake pad 34 are not in contact with the link arm 21, and a position (c) where the first brake pad 33 and the second brake pad 34 sandwich at least a portion of the disk 31.

When a distance between the first joint 23 and a center of a region P on which the brake 32 presses the disk 31 is defined as a "distance D", a brake torque by the braking mechanism 3 is a multiplier of the distance D and a frictional force generated on the disk 31. Here, the frictional force generated on the disk 31 is a frictional force generated between the disk 31 and the first brake pad 33 and the second brake pad 34.

The brake 32 is disposed at a position where the distance D becomes longer as the disk 31 rotates about the first joint 23 in the first rotation direction R1.

[Operation of Holding Device 100]

Next, an operation of the holding device 100 will be described by taking a case where a holding target of the holding device 100 is an endoscope E as an example.

The surgeon provides a hole (insertion point of a body wall) for installing a trocar T in an abdomen B of a patient, and punctures the trocar T in the hole. The surgeon moves the holding device 100 closer to the patient, activates the lock mechanism 12 of the base 1, and fixes the position of the base 1. Next, the surgeon introduces an insertion portion E1 of the endoscope E held by the holder 2a of the holding device 100 into an abdominal cavity through the trocar T punctured in the abdomen B of the patient.

The surgeon manually moves the holder 2a of the arm 2 so that the medical device is disposed at an intended position. The surgeon rotates the endoscope E held so that the medical device faces the intended direction. The first joint 23 and the second joint 24 of the arm 2 rotate as the surgeon moves the endoscope E. The endoscope E inserted into the abdominal cavity through the trocar T is configured to turn with respect to the body wall. Here, a turning center of the endoscope E inserted into the abdominal cavity through the trocar T is defined as a "pivot point PP".

Figure 4:
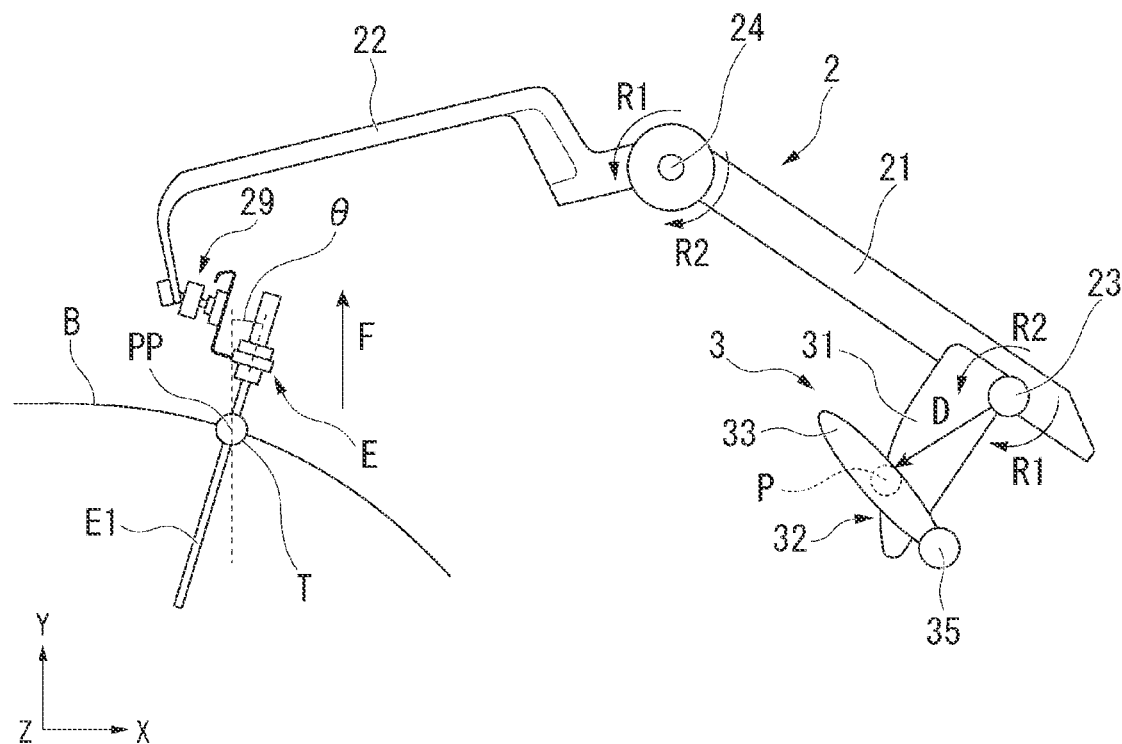
FIG. 4 is a side view of an arm and a braking mechanism in which a holder of the holding device is moved in a direction away from a base.

FIG. 4 is a side view of the arm 2 and the braking mechanism 3 in which the holder 2a is moved in a direction away from the base 1. The first joint 23 and the second joint 24 rotate in the second rotation direction R2. Since the distance between the trocar T and the base 1 is fixed, by moving the holder 2a in the direction away from the base 1, the direction of the insertion portion E1 of the endoscope E approaches the vertical direction (Y-axis direction). As a result, a tilt angle θ of the insertion portion E1 of the endoscope E with respect to the vertical direction decreases.

Since a portion of the disk 31 is sandwiched between the first brake pad 33 and the second brake pad 34, the rotation of the link arm 21 is braked. A brake torque by the braking mechanism 3 is larger than a moment generated by the external force (repulsive force) F received by the endoscope E from the abdomen B, and thus, the endoscope E is suitably held at the disposed position.

The surgeon applies an external force having a predetermined value or greater to the holder 2a or the portion interlocking with the holder 2a to generate a moment exceeding the brake torque by the braking mechanism 3, and thereby the surgeon can move the endoscope E held by the holder 2a to a different position. Since a predetermined force or greater is required to move the endoscope E to a different position, an unintended moving operation of the endoscope E is unlikely to occur. Since an initial motion speed when moving the endoscope E to a different position is limited, it is unlikely that an operation error by the surgeon will occur.

Figure 5:
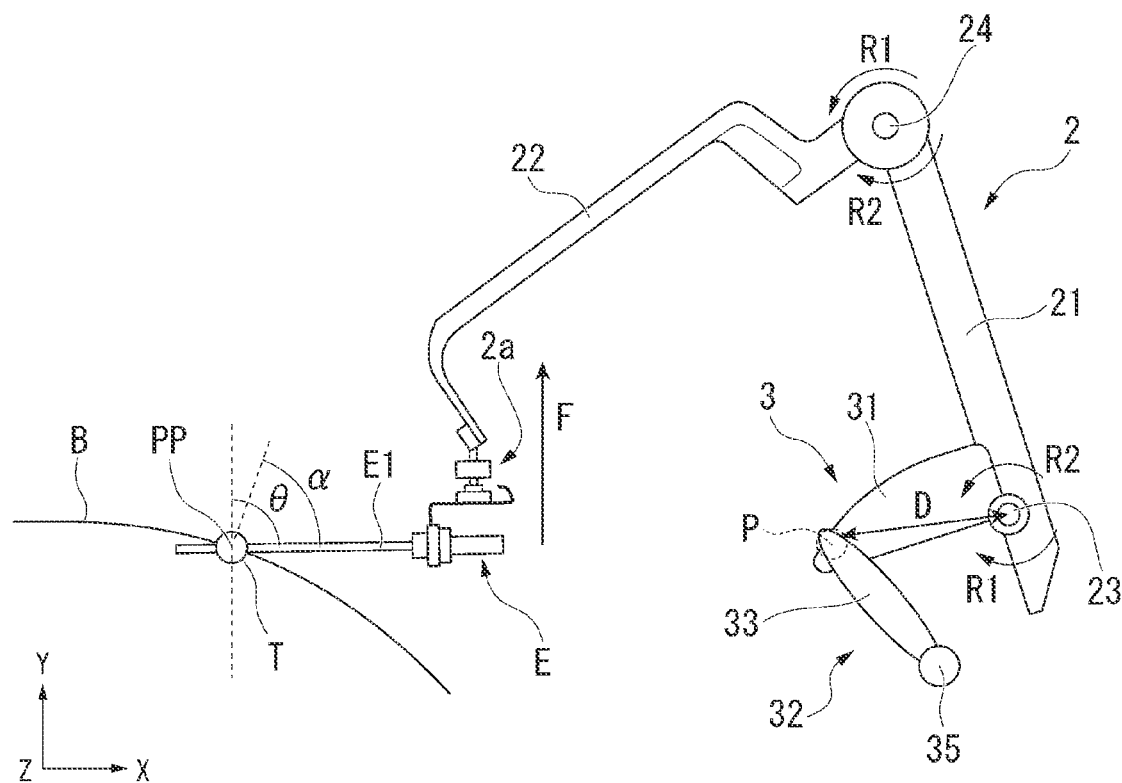
FIG. 5 is a side view of the arm and the braking mechanism in which the holder of the holding device is moved in a direction approaching the base.

FIG. 5 is a side view of the arm 2 and the braking mechanism 3 in which the holder 2a is moved in a direction approaching the base 1. The first joint 23 and the second joint 24 rotate in the first rotation direction R1. Since the distance between the trocar T and the base 1 is fixed, by moving the holder 2a in the direction approaching the base 1, the direction of the insertion portion E1 of the endoscope E becomes close to the horizontal direction (X-axis direction). As a result, the tilt angle θ of the insertion portion E1 of the endoscope E with respect to the vertical direction increases.

Even when the tilt angle θ increases, as shown in FIG. 5, since a portion of the disk 31 is sandwiched between the first brake pad 33 and the second brake pad 34, the rotation of the link arm 21 is braked. The brake torque by the braking mechanism 3 is larger than the moment generated by the external force F received by the endoscope E from the abdomen B, and the medical device is suitably held at the disposed position.

When the tilt angle θ increases, as shown in FIG. 5, the link arm 21 rotates in the first rotation direction R1 with respect to the base 1. The distance D between the center of the region P on which the brake 32 presses the disk 31 and the first joint 23 increases. That is, the distance D is changed depending on a rotation angle of the first joint 23. As a result, the brake torque of the braking mechanism 3 becomes larger than the brake torque of the braking mechanism 3 when the tilt angle θ decreases as shown in FIG. 4.

As shown in FIG. 5, when the tilt angle θ increases and a direction of the insertion portion E1 of the endoscope E becomes close to the horizontal direction, the patient is in a suspine posture, and thus, an angle α between a longitudinal axis of the endoscope E and a normal line of the body wall at the pivot point PP also increases. As a result, the external force F that the endoscope E receives from the abdomen B increases. Even in this case, since the brake torque of the braking mechanism 3 is larger than the brake torque of the braking mechanism 3 when the tilt angle θ shown in FIG. 4 is small, the endoscope E is suitably held at the disposed position.

As shown in FIG. 5, when the tilt angle θ increases and a direction of the insertion portion E1 of the endoscope becomes close to the horizontal direction, the angle α also increases and a probability that the insertion portion E1 comes into contact with the body wall increases. However, since the brake torque of the braking mechanism 3 increases when the tilt angle θ shown in FIG. 5 increases, it is possible to suitably prevent the insertion portion E1 from coming into contact with the body wall.

When the insertion portion E1 of the endoscope E is moved in the direction in which the tilt angle θ increases, the link arm 21 rotates in the first rotation direction R1 with respect to the base 1, and the brake torque of the braking mechanism 3 increases. Meanwhile, when the insertion portion E1 of the endoscope E is moved in the direction in which the tilt angle θ decreases, the link arm 21 rotates in the second rotation direction R2 with respect to the base 1, and the brake torque of the braking mechanism 3 decreases. That is, the surgeon is capable of more easily moving the insertion portion E1 of the endoscope E in the direction in which the tilt angle θ decreases than in the direction in which the tilt angle θ increases.

According to the holding device 100 of the present embodiment, it is possible to fix the position of the holding endoscope E without performing a separate operation. In the braking mechanism 3, the brake torque for braking the rotation of the arm 2 is varied according to the position of the endoscope E to be held.

According to the holding device 100 of the present embodiment, even when the tilt angle θ of the insertion portion E1 of the endoscope E with respect to the vertical direction increases and the external force F received by the endoscope E from the abdomen B increases, the brake torque of the braking mechanism 3 increases, and thus, the endoscope E is capable of being suitably held.

The insertion portion E1 of the endoscope E is introduced into the abdominal cavity through the trocar T. The distance between the trocar T and the base 1 is fixed during a procedure. Therefore, a posture of the arm 2 is capable of being roughly estimated from the tilt angle θ, although there is a difference depending on the position of the trocar T. When a rotation angle of the first joint 23 corresponding to the tilt angle θ is calculated and the distance D corresponding to the rotation angle of the first joint 23 is adjusted according to the position or shape of the disk 31, it is possible to generate a desired brake torque corresponding to the tilt angle θ.

As described above, the first embodiment of is described in detail with reference to the drawings. However, specific configurations are not limited to the embodiment, and include a design modification or the like within a scope which does not depart from the gist of the present invention. In addition, components shown in the above-described first embodiment and modification examples shown below can be appropriately combined and configured.

Modification Example 1

For example, in the above embodiment, the braking mechanism 3 is the disk brake mechanism having the disk 31 and a brake 32. However, an aspect of the braking mechanism is not limited to this. The braking mechanism may be any mechanism as long as the brake torque increases as the link arm 21 rotates about the first joint 23 in the first rotation direction R1.

Second Embodiment

A holding device according to a second embodiment will be described with reference to FIGS. 6 to 9. In the following descriptions, the same components as those already described are denoted by the same reference numerals, and repeated descriptions will be omitted. A holding device 100B according to the second embodiment has a different degree of freedom of the arm as compared with the holding device 100 according to the first embodiment. The holding device 100B includes the base 1, an arm 2B, and a braking mechanism 3B.

Figure 6:
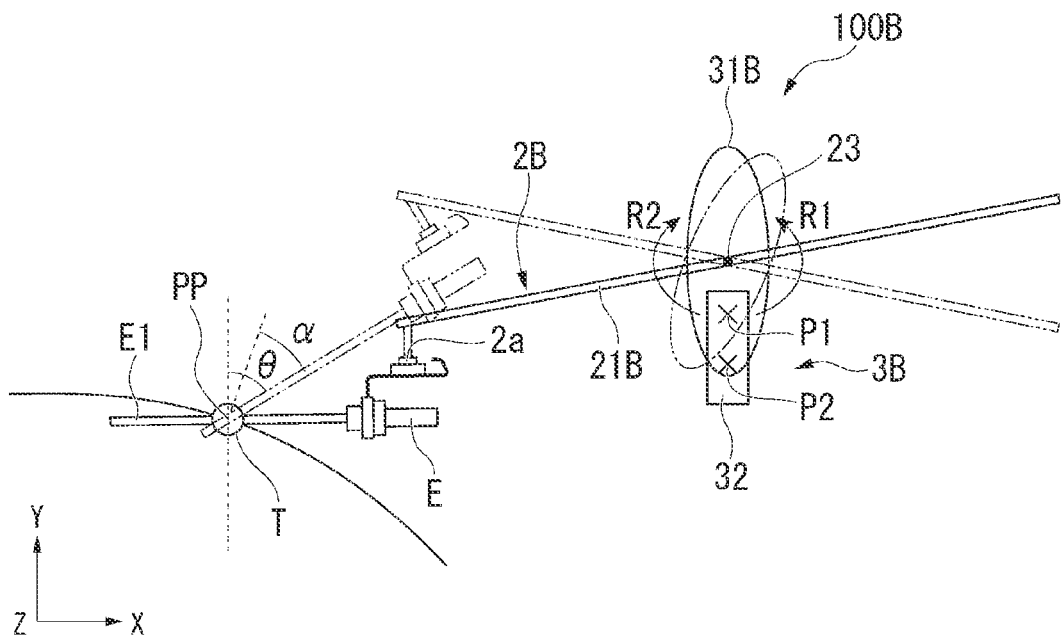
FIG. 6 is a side view of an arm and a braking mechanism of a holding device according to a second embodiment.

FIG. 6 is a side view of the arm 2B and the braking mechanism 3B.

The arm 2B has a link arm 21B and the first joint 23. The first joint 23 rotatably connects the link arm 21B and the base 1. The arm 2B is a so-called one-degree-of-freedom arm mechanism having one joint.

The link arm (first arm) 21B is rotatably supported by the base 1 by the first joint 23 on a proximal end side. The link arm 21B has the holder 2a at a distal end of the link arm 21B. The holder 2a is configured to hold the medical device.

The braking mechanism 3B is a disk brake mechanism having a disk 31B attached to the link arm 21B and a brake 32 attached to the base 1.

Figure 7:
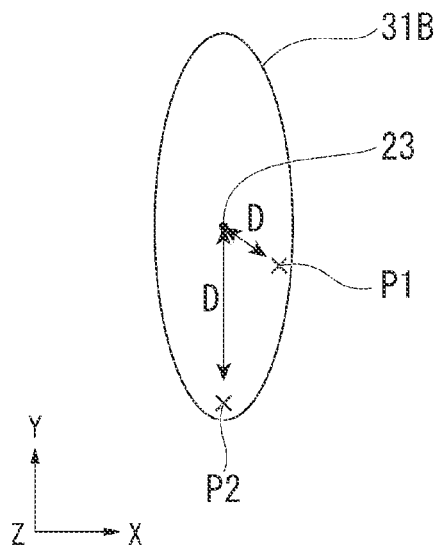
FIG. 7 is a side view of a disk of the holding device.

FIG. 7 is a side view of the disk 31B.

The disk 31B is a plate-shaped member. The disk 31B is attached to the link arm 21B. The disk 31B rotates together with the link arm 21B with the first joint 23 as a center of rotation. The disk 31B is attached to the link arm 21B so that a plate thickness direction coincides with the direction of the rotation axis of the first joint 23.

As shown in FIG. 7, the disk 31B has an elliptical shape whose center is located at the first joint 23 when viewed in the plate thickness direction (Z-axis direction).

The brake 32 is attached to the base 1, and a relative position between the brake 32 and the first joint 23 attached to the base 1 is not changed. Even when the link arm 21B rotates about the first joint 23 within an assumed range of use, the brake 32 is disposed at a position (a) where the biasing unit 35 does not come into contact with the disk 31B, a position (b) where the first brake pad 33 and the second brake pad 34 are not in contact with the link arm 21B, and a position (c) where the first brake pad 33 and the second brake pad 34 sandwich at least a portion of the disk 31B.

When a distance between the first joint 23 and a center of a region P on which the brake 32 presses the disk 31B is defined as a "distance D", a brake torque by the braking mechanism 3 is a multiplier of the distance D and a frictional force generated on the disk 31B. Here, the frictional force generated on the disk 31B is a frictional force generated between the first brake pad 33, the second brake pad 34, and the disk 31B.

The brake 32 is disposed at a position where the distance D becomes longer as the disk 31B rotates about the first joint 23 in the first rotation direction R1.

Next, an operation of the holding device 100B will be described by taking a case where a holding target of the holding device 100B is the endoscope E as an example. The insertion portion E1 of the endoscope E is introduced into the abdominal cavity through the trocar T punctured in the abdomen B of the patient.

The surgeon moves the endoscope E and the arm 2B shown by broken lines in FIG. 6 in a direction in which a holder 2a approaches the base 1 as shown by solid lines. The first joint 23 rotates in the first rotation direction R1. Since the distance between the trocar T and the base 1 is fixed, by moving the holder 2a in the direction approaching the base 1, the direction of the insertion portion E1 of the endoscope E becomes close to the horizontal direction (X-axis direction). As a result, the tilt angle θ of the insertion portion E1 of the endoscope E with respect to the vertical direction increases.

When the tilt angle θ increases, as shown in FIG. 6, the link arm 21B rotates in the first rotation direction R1 with respect to the base 1. As shown in FIG. 7, the center of the region P on which the brake 32 presses the disk 31 moves from a center P1 to a center P2. The distance D between the center of the region P on which the brake 32 presses the disk 31B and the first joint 23 becomes long. As a result, the brake torque of the braking mechanism 3 becomes larger than the brake torque of the braking mechanism 3 when the tilt angle θ decreases.

Figure 8:
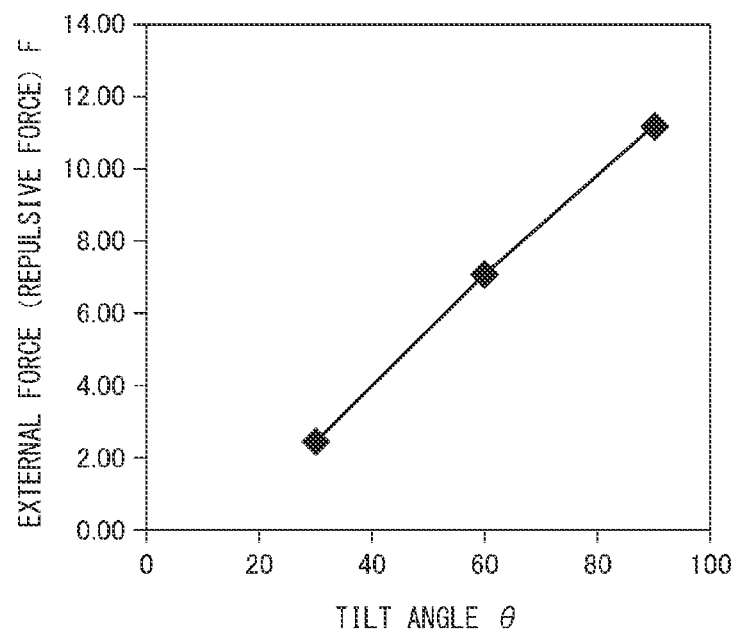
FIG. 8 is a graph showing a relationship between a tilt angle of the holding device and an external force.

FIG. 8 is a graph showing a relationship between the tilt angle θ and the external force (repulsive force) F that the endoscope E receives from the abdomen B. When the tilt angle θ increases and a direction of the insertion portion E1 of the endoscope E becomes close to the horizontal direction, the external force F received by the endoscope E from the abdomen B increases in proportion to the tilt angle θ (F=K*θ[N]).

Figure 9:
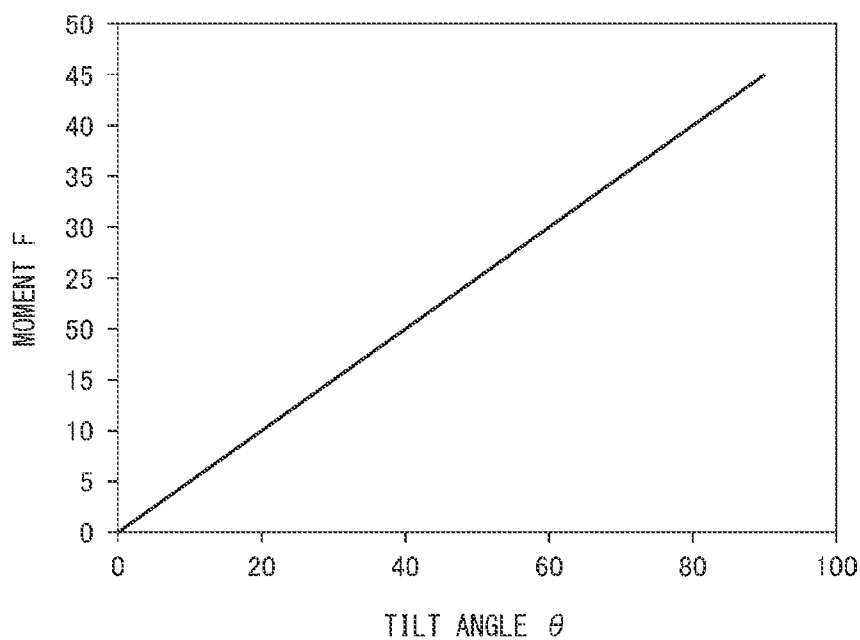
FIG. 9 is a graph showing a relationship between the tilt angle of the holding device and a moment generated by the external force.

FIG. 9 is a graph showing a relationship between the tilt angle θ and a moment M generated by the external force F. The moment M increases in proportion to the external force F (M=L*F[N]). When the tilt angle θ increases and a direction of the insertion portion E1 of the endoscope E becomes close to the horizontal direction, the external force F received by the endoscope E from the abdomen B increases, and the rotational moment M increases. Even in this case, since the brake torque of the braking mechanism 3 is larger than the brake torque of the braking mechanism 3 when the tilt angle θ is small as shown in FIG. 4, the endoscope E is capable of being suitably held at the disposed position.

According to the holding device 100B of the present embodiment, it is possible to fix the position of the holding endoscope E without performing a separate operation. In the braking mechanism 3B, the brake torque for braking the rotation of the arm 2B is varied according to the position of the endoscope E to be held.

According to the holding device 100B of the present embodiment, even when the tilt angle θ of the insertion portion E1 of the endoscope E with respect to the vertical direction increases and the external force F received by the endoscope E from the abdomen B increases, the brake torque of the braking mechanism 3B increases, and thus, the endoscope E is capable of being suitably held.

As described above, the second embodiment is described in detail with reference to the drawings. However, specific configurations are not limited to the embodiment, and include a design modification or the like within a scope which does not depart from the gist of the present invention. In addition, components shown in the above-described second embodiment and modification examples of the first embodiment can be appropriately combined and configured.

Modification Example 2

For example, in the above embodiment, the disk 31B has an elliptical shape whose center is located at the first joint 23 when viewed in the plate thickness direction (Z-axis direction), but the shape of the disk is not limited to this. The disk may be formed by cutting a portion of the elliptical shape that does not come into contact with the brake 32.

Third Embodiment

A holding device according to a third embodiment will be described with reference to FIGS. 10 to 14. In the following description, the same components as those already described are denoted by the same reference numerals, and repeated descriptions will be omitted. A holding device 100C according to the third embodiment has a different disk aspect as compared with the holding device 100B according to the second embodiment. The holding device 100C includes the base 1, the arm 2B, and a braking mechanism 3C.

Figure 10:
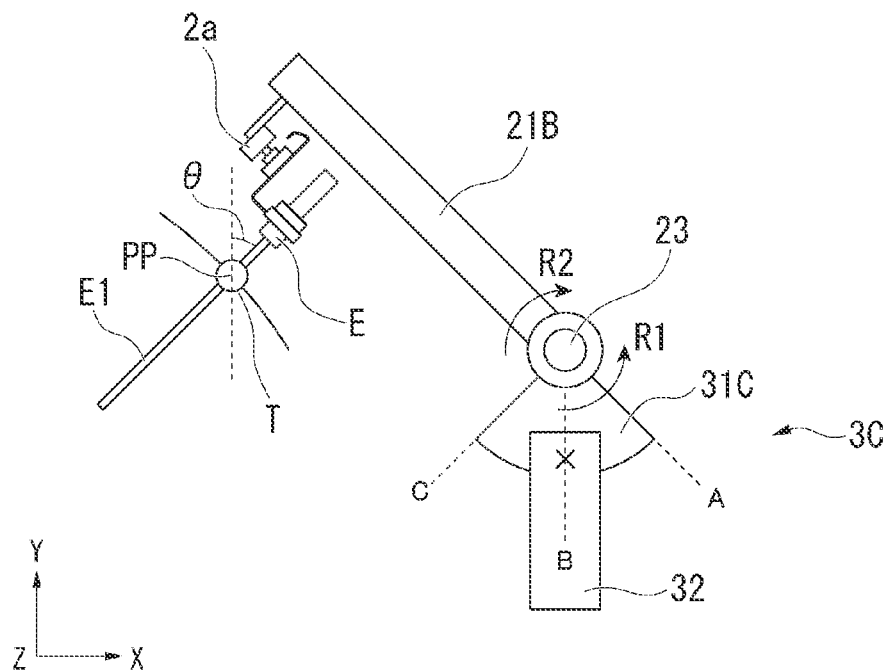
FIG. 10 is a side view of a braking mechanism of a holding device according to the third embodiment.

FIG. 10 is a side view of the braking mechanism 3C.

The braking mechanism 3C is a disk brake mechanism having a disk 31C attached to the link arm 21B and the brake 32 attached to the base 1.

The disk 31C is a plate-shaped member. The disk 31C is attached to the link arm 21B and rotates together with the link arm 21B with the first joint 23 as the center of rotation. The disk 31C is attached to the link arm 21B so that a plate thickness direction coincides with the direction of the rotation axis of the first joint 23.

Figure 11:
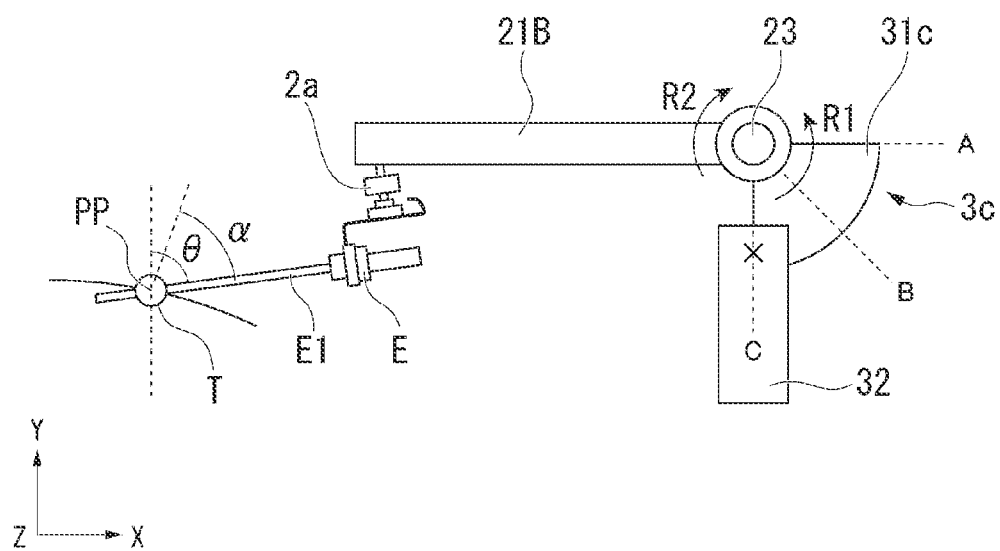
FIG. 11 is a side view of an arm and a braking mechanism in which a holder of the holding device is moved in a direction approaching to a base.

FIG. 11 is a side view of the arm 2B and the braking mechanism 3C in which the holder 2a is moved in the direction approaching the base 1. The first joint 23 rotates in the first rotation direction R1. Since the distance between the trocar T and the base 1 is fixed as in the second embodiment, the direction of the insertion portion E1 of the endoscope E becomes close to the horizontal direction by moving the holder 2a in the direction approaching the base 1. The tilt angle θ of the insertion portion E1 of the endoscope E with respect to the vertical direction increases.

Figure 12:
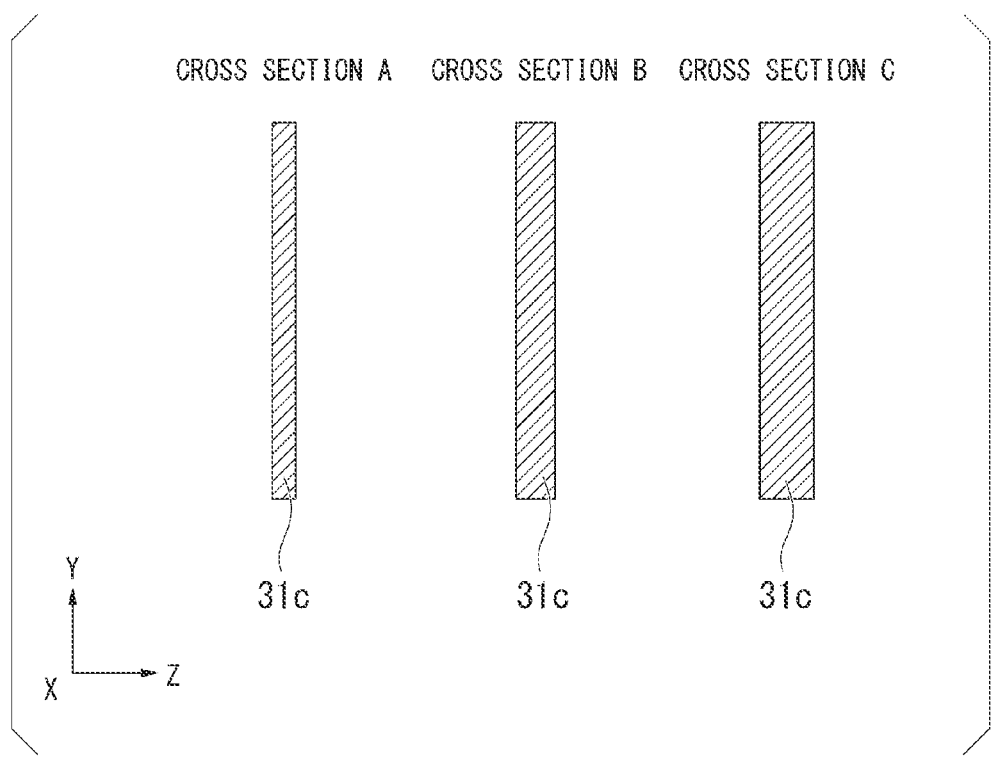
FIG. 12 is a cross-sectional view showing cross sections A, B, and C of a disk of the holding device in a plate thickness direction.

FIG. 12 is a cross-sectional view showing cross sections A, B, and C of the disk 31C shown in FIGS. 10 and 11 in the plate thickness direction. As shown in FIG. 12, a thickness of the disk 31C in the plate thickness direction (Z-axis direction) is varied along the rotation direction of the first joint 23. Specifically, the thickness of the disk 31C in the plate thickness direction (Z-axis direction) increases along the second rotation direction R2 (thickness of cross section A<thickness of cross section B<thickness of cross section C).

Figure 13:
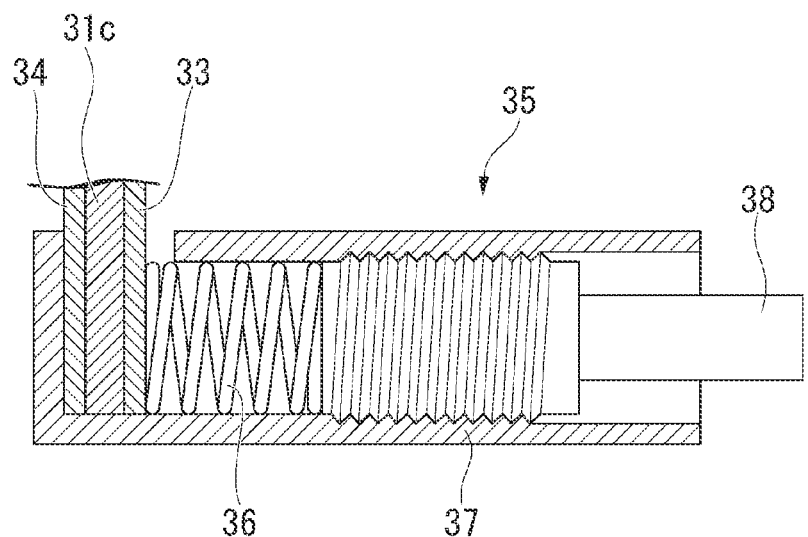
FIG. 13 is a cross-sectional view of a brake that presses the cross section B of the disk of the holding device.

Next, an operation of the holding device 100C will be described by taking a case where a holding target of the holding device 100C is the endoscope E as an example. The insertion portion E1 of the endoscope E is introduced into the abdominal cavity through the trocar T punctured in the abdomen B of the patient. The endoscope E and the arm 2B are held by the holder 2a as shown in FIG. 10, and the brake 32 presses the cross section B of the disk 31C. FIG. 13 is a cross-sectional view of the brake 32 that presses the cross section B of the disk 31C.

The surgeon moves the endoscope E and the arm 2B in a direction in which the holder 2a approaches the base 1 as shown in FIG. 11. The first joint 23 rotates in the first rotation direction R1. Since the distance between the trocar T and the base 1 is fixed, the direction of the insertion portion E1 of the endoscope E becomes close to the horizontal direction by moving the holder 2a in the direction approaching the base 1. As a result, the tilt angle θ of the insertion portion E1 of the endoscope E with respect to the vertical direction increases.

Figure 14:
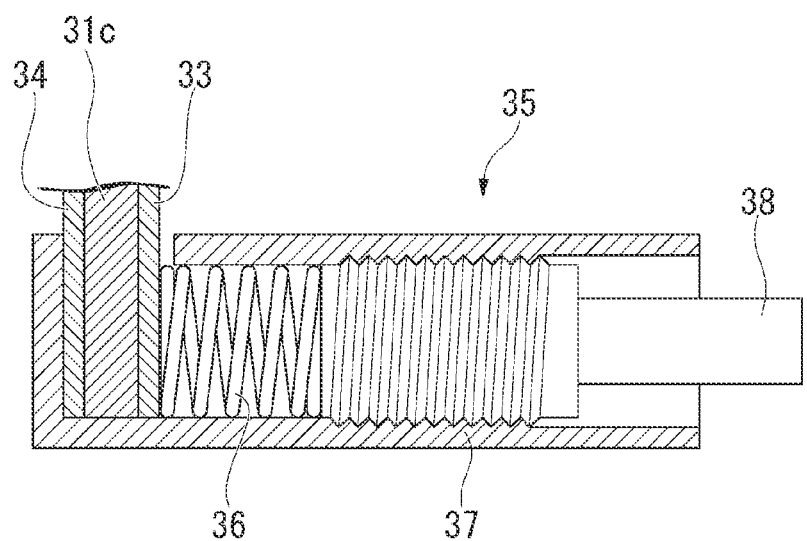
FIG. 14 is a cross-sectional view of a brake that presses a cross section C of the disk of the holding device.

When the tilt angle θ increases, as shown in FIG. 11, the link arm 21B rotates in the first rotation direction R1 with respect to the base 1. The brake 32 presses the cross section C of the disk 31C. FIG. 14 is a cross-sectional view of the brake 32 that presses the cross section C of the disk 31C. The thickness of the cross section of the region P on which the brake 32 presses the disk 31 increases. The distance D between the center of the region P on which the brake 32 presses the disk 31B and the first joint 23 increases. As a result, the brake torque of the braking mechanism 3 becomes larger than the brake torque of the braking mechanism 3 when the tilt angle θ decreases.

When the tilt angle θ increases and a direction of the insertion portion E1 of the endoscope E becomes close to the horizontal direction, the external force F received by the endoscope E from the abdomen B increases. Even in this case, since the brake torque of the braking mechanism 3C is larger than the brake torque of the braking mechanism 3 when the tilt angle θ is small, the endoscope E is capable of being suitably held at the disposed position.

According to the holding device 100C of the present embodiment, it is possible to fix the position of the holding endoscope E without performing a separate operation. In the braking mechanism 3C, the brake torque for braking the rotation of the arm 2B is varied according to the position of the endoscope E to be held.

According to the holding device 100C of the present embodiment, even when the tilt angle θ of the insertion portion E1 of the endoscope E with respect to the vertical direction increases and the external force F received by the endoscope E from the abdomen B increases, the brake torque of the braking mechanism 3C increases, and thus, the endoscope E is capable of being suitably held.

As described above, the third embodiment is described in detail with reference to the drawings. However, specific configurations are not limited to the embodiment, and include a design modification or the like within a scope which does not depart from the gist of the present invention. In addition, components shown in the above-described third embodiment and modification examples of the first embodiment can be appropriately combined and configured.

Modification Example 3

For example, in the above embodiment, the thickness of the disk 31C in the plate thickness direction (Z-axis direction) increases along the second rotation direction R2, but the aspect of the disk is not limited to this. For example, a friction coefficient may be varied for each place pressed by the brake 32 depending on a processing aspect of a surface of the disk.

Fourth Embodiment

A holding device according to a fourth embodiment will be described with reference to FIGS. 15 and 16. In the following description, the same components as those already described are denoted by the same reference numerals, and repeated descriptions will be omitted. A holding device 100D according to the fourth embodiment has a different attachment aspect of the braking mechanism as compared with the holding device 100 according to the first embodiment.

Figure 15:
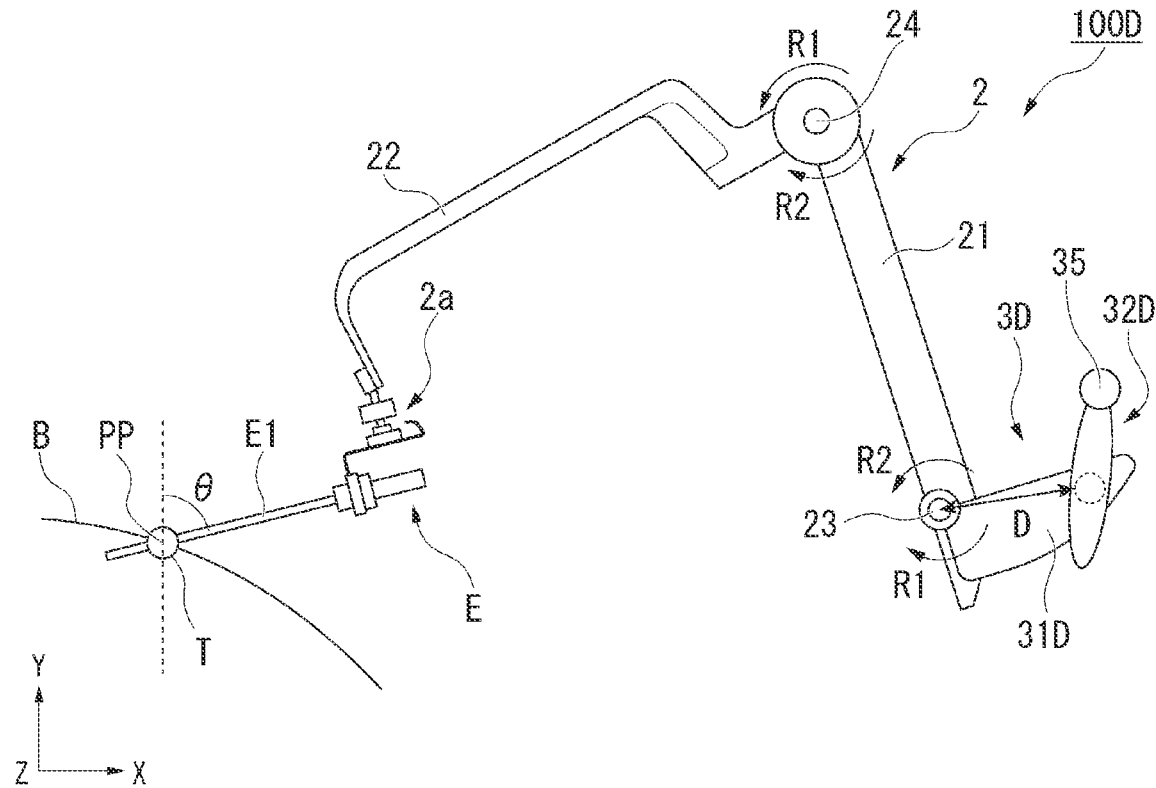
FIG. 15 is a side view of a braking mechanism of a holding device according to a fourth embodiment.

FIG. 15 is a side view of the holding device 100D.

The holding device 100D includes a base 1, the arm 2, and a braking mechanism 3D.

The braking mechanism 3D is a disk brake mechanism having a disk 31D attached to the link arm 21 and a brake 32D attached to the base 1.

The disk 31D is attached to the link arm 21 and rotates together with the link arm 21 with the first joint 23 as a center of rotation. The disk 31 is attached to the link arm 21 so that a plate thickness direction coincides with the direction of the rotation axis of the first joint 23.

As shown in FIG. 15, the disk 31D is attached to a side opposite to the link arm 21 with respect to the disk 31 of the first embodiment in an XY plane including an X-axis and a Y-axis.

The brake 32D sandwiches the disk 31D from both surfaces and brakes the rotation of the link arm 21 to which the disk 31D is attached. The brake 32D has the first brake pad 33, the second brake pad 34, and the biasing unit 35.

The brake 32D is attached to the base 1, and a relative position between the brake 32D and the first joint 23 attached to the base 1 is not changed. Even when the link arm 21 rotates about the first joint 23 within an assumed range of use, the brake 32D is disposed at a position (a) where the biasing unit 35 does not come into contact with the disk 31D, a position (b) where the first brake pad 33 and the second brake pad 34 are not in contact with the link arm 21, and a position (c) where the first brake pad 33 and the second brake pad 34 sandwich at least a portion of the disk 31D.

The brake 32D is disposed at a position where the distance D becomes longer as the disk 31D rotates about the first joint 23 in the second rotation direction R2.

[Operation of Holding Device 100D]

Next, an operation of the holding device 100D will be described by taking a case where a holding target of the holding device 100D is the endoscope E as an example. As shown in FIG. 15, the insertion portion E1 of the endoscope E is introduced into the abdominal cavity through the trocar T punctured in the abdomen B of the patient. The surgeon manually moves the holder 2a of the arm 2 in order to further introduce the insertion portion E1 of the endoscope E into the abdominal cavity while keeping the tilt angle θ of the insertion portion E1 of the endoscope E with respect to the vertical direction constant.

Figure 16:
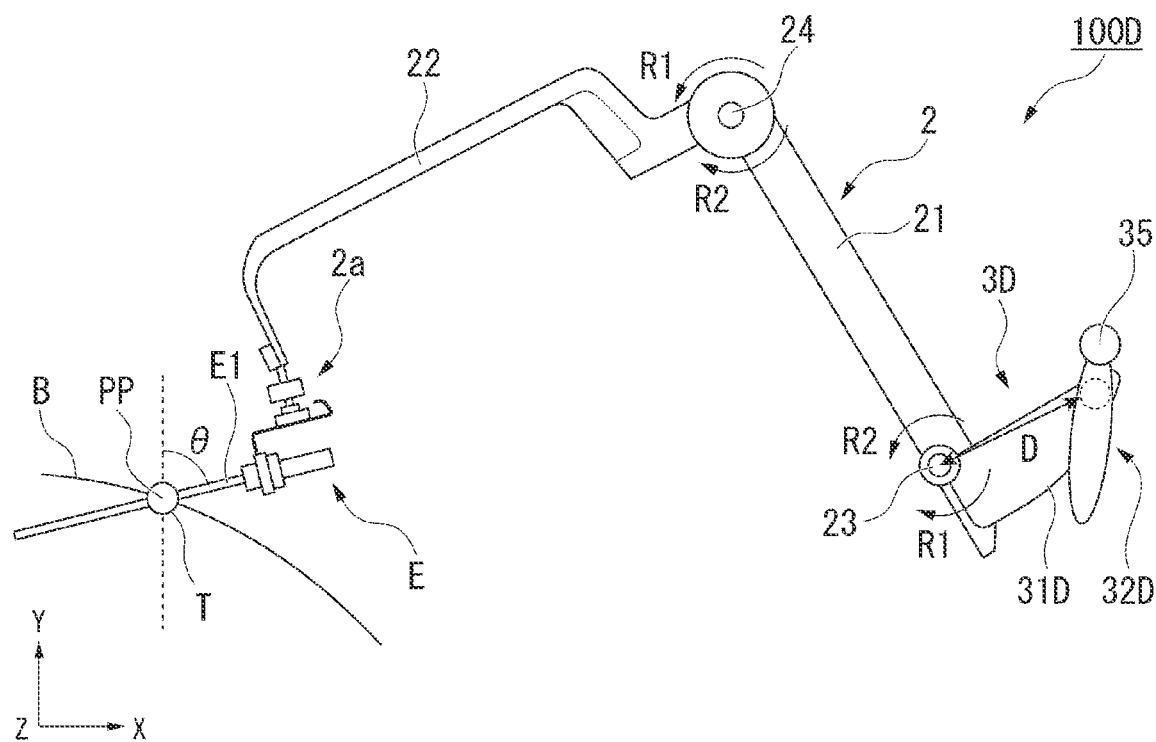
FIG. 16 is a side view of an arm and a braking mechanism in which a holder of the holding device is moved in a direction approaching a base.

FIG. 16 is a side view of the arm 2 and the braking mechanism 3D in which the holder 2a is moved in a direction away from the base 1. The first joint 23 and the second joint 24 rotate in the second rotation direction R2, and an amount of insertion of the insertion portion E1 of the endoscope E into the abdominal cavity increases. The distance D between the center of the region P on which the brake 32D presses the disk 31D and the first joint 23 becomes long. That is, the distance D is varied depending on the rotation angle of the first joint 23. As a result, the brake torque of the braking mechanism 3D is larger than the brake torque of the braking mechanism 3D when the insertion amount of the insertion portion E1 into the abdominal cavity is small as shown in FIG. 15.

According to the holding device 100D of the present embodiment, it is possible to fix the position of the holding endoscope E without performing a separate operation. In the braking mechanism 3D, the brake torque for braking the rotation of the arm 2 is varied according to the position of the endoscope E to be held.

According to the holding device 100D of the present embodiment, as the insertion amount of the insertion portion E1 of the endoscope E increases, the brake torque of the braking mechanism 3D increases. Therefore, it is possible to suitably prevent the insertion portion E1 of the endoscope E from being inserted in excess of an intended insertion amount.

What is claimed is:

1. A holding device for holding a medical device, comprising:
   an arm having a holder positioned at a distal end of the arm, and configured to hold the medical device;
   a base configured to rotatably support the arm by a first joint;
   a disk attached to the arm; and
   a brake attached to the base and configured to press the disk,
   wherein a distance between a rotation center of the disk and a region where the brake presses the disk is changed depending on a rotation angle of the first joint.

2. The holding device according to claim 1, wherein when the disk moves the arm in a direction in which the holder approaches the base, the brake is disposed at a position where the distance increases as the first joint rotates in a direction of rotation.

3. The holding device according to claim 1, wherein the distance is changed in proportion to the rotation angle of the first joint.

4. The holding device according to claim 1, wherein the arm further includes a second joint disposed between the holder and the first joint.

5. The holding device according to claim 1, wherein when the holding device is configured to hold the medical device so as to be turnable with respect to a body wall when the medical device is inserted into the body wall.

6. The holding device according to claim 5, wherein the brake is disposed at a position where the distance increases according to an amount of insertion when the medical device is inserted into the body by the arm.

7. The holding device according to claim 5, wherein the medical device is inserted into the body via a trocar.

8. The holding device according to claim 5, wherein the brake is disposed at a position where the distance increases according to an angle between a normal line from the body wall and a longitudinal axis of the medical device at a pivot point which is a turning center.

9. The holding device according to claim 8, wherein the pivot point is an insertion point of the body wall.

* * * * *